US009717611B2

(12) United States Patent
Jensen et al.

(10) Patent No.: US 9,717,611 B2
(45) Date of Patent: Aug. 1, 2017

(54) STENT GRAFT AND INTRODUCER ASSEMBLY

(75) Inventors: Kim Moegelvang Jensen, Koebenhavn (DK); Bent Oehlenschlaeger, Skensved (DK); Erik Rasmussen, Slagelse (DK); Steven J. Charlebois, West Lafayette, IN (US); William K. Dierking, Louisville, KY (US); Jarin Kratzberg, Lafayette, IN (US); Blayne A. Roeder, Lafayette, IN (US); Richard A. Swift, South Bend, IN (US); Sharath Gopalakrishnamurthy, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 68 days.

(21) Appl. No.: 12/946,238

(22) Filed: Nov. 15, 2010

(65) Prior Publication Data
US 2011/0125249 A1 May 26, 2011

(30) Foreign Application Priority Data
Nov. 19, 2009 (GB) .................................. 0920327.4

(51) Int. Cl.
*A61F 2/07* (2013.01)
*A61F 2/95* (2013.01)
(Continued)

(52) U.S. Cl.
CPC .................. *A61F 2/95* (2013.01); *A61F 2/07* (2013.01); *A61F 2/86* (2013.01); *A61F 2/89* (2013.01);
(Continued)

(58) Field of Classification Search
CPC ........... A61F 2/07–2002/007; A61F 2/95–2/97
(Continued)

(56) References Cited

U.S. PATENT DOCUMENTS 5,258,021 A 11/1993 Duran
5,292,331 A 3/1994 Boneau
(Continued)

FOREIGN PATENT DOCUMENTS

EP 0686379 A2 12/1995
EP 0960607 A1 12/1999
(Continued)

OTHER PUBLICATIONS

PCT/US2010/056673 Search Report, MED Institute, Inc, May 6, 2011.
(Continued)

*Primary Examiner* — Yashita Sharma
*Assistant Examiner* — Rebecca Preston
(74) *Attorney, Agent, or Firm* — Brinks Gilson & Lione

(57) ABSTRACT

A stent graft (40) for treating Type-A dissections in the ascending aorta (22) is provided with a plurality of diameter reducing suture loops (56-60) operable to constrain the stent graft during deployment thereof in a patient's aorta. The diameter reducing loops (56-60) allow the stent graft (40) to be partially deployed, in such a manner that its location can be precisely adjusted in the patient's lumen. In this manner, the stent graft can be placed just by the coronary arteries (26, 28) with confidence that these will not be blocked. The stent graft (40) is also provided with proximal and distal bare stents (44,52) for anchoring purposes.

19 Claims, 8 Drawing Sheets

(51) Int. Cl.
- *A61F 2/86* (2013.01)
- *A61F 2/966* (2013.01)
- *A61F 2/89* (2013.01)
- *A61F 2/915* (2013.01)

(52) U.S. Cl.
CPC .............. *A61F 2/915* (2013.01); *A61F 2/966* (2013.01); *A61F 2002/075* (2013.01); *A61F 2002/9517* (2013.01); *A61F 2230/0013* (2013.01); *A61F 2230/0078* (2013.01)

(58) Field of Classification Search
USPC ...................................... 623/1.11–1.13, 1.23
See application file for complete search history.

(56) References Cited

U.S. PATENT DOCUMENTS

| | | |
|---|---|---|
| 5,403,341 A | 4/1995 | Solar |
| 5,569,295 A | 10/1996 | Lam .............................. 606/198 |
| 5,607,468 A | 3/1997 | Rogers et al. |
| 5,630,829 A | 5/1997 | Lauterjung |
| 5,674,278 A | 10/1997 | Boneau |
| 5,749,921 A | 5/1998 | Lenker et al. |
| 5,782,904 A | 7/1998 | White et al. |
| 5,843,164 A | 12/1998 | Frantzen et al. .................... 623/1 |
| 5,855,601 A | 1/1999 | Bessler et al. |
| 5,906,639 A | 5/1999 | Rudnick et al. |
| 5,913,897 A | 6/1999 | Corso, Jr. et al. ................. 623/1 |
| 5,961,546 A | 10/1999 | Robinson et al. |
| 5,993,482 A | 11/1999 | Chuter |
| 6,071,307 A | 6/2000 | Rhee et al. ................... 623/1.13 |
| 6,110,198 A | 8/2000 | Fogarty et al. |
| 6,203,569 B1 | 3/2001 | Wijay |
| 6,245,102 B1 | 6/2001 | Jayaraman |
| 6,287,315 B1 | 9/2001 | Wijeratne et al. |
| 6,293,966 B1 | 9/2001 | Frantzen |
| 6,296,662 B1 | 10/2001 | Caffey |
| 6,336,937 B1 | 1/2002 | Vonesh et al. |
| 6,346,118 B1 | 2/2002 | Baker et al. .................. 623/1.12 |
| 6,348,068 B1 | 2/2002 | Campbell et al. ............ 623/2.36 |
| 6,350,277 B1 | 2/2002 | Kocur .......................... 623/1.11 |
| 6,368,345 B1 | 4/2002 | Dehdashtian et al. ....... 623/1.13 |
| 6,423,090 B1 | 7/2002 | Hancock ...................... 623/1.15 |
| 6,451,051 B2 | 9/2002 | Drasler et al. |
| 6,471,722 B1 | 10/2002 | Inoue |
| 6,514,282 B1 | 2/2003 | Inoue ........................... 623/1.13 |
| 6,524,335 B1 | 2/2003 | Hartley et al. ............... 623/1.13 |
| 6,539,984 B2 | 4/2003 | Lam |
| 6,551,350 B1 | 4/2003 | Thornton et al. |
| 6,579,314 B1 | 6/2003 | Lombardi et al. ........... 623/1.44 |
| 6,582,458 B1 | 6/2003 | White et al. ................. 623/1.11 |
| 6,585,757 B1 | 7/2003 | Callol |
| 6,592,614 B2 | 7/2003 | Lenker et al. |
| 6,616,689 B1 | 9/2003 | Ainsworth et al. .......... 623/1.16 |
| 6,629,994 B2 | 10/2003 | Gomez et al. ............... 623/1.15 |
| 6,635,083 B1 | 10/2003 | Cheng et al. ................ 623/1.15 |
| 6,645,242 B1 | 11/2003 | Quinn |
| 6,648,911 B1 | 11/2003 | Sirhan et al. ................ 623/1.15 |
| 6,663,661 B2 | 12/2003 | Boneau |
| 6,673,102 B1 | 1/2004 | Vonesh et al. |
| 6,695,875 B2* | 2/2004 | Stelter et al. ................ 623/1.13 |
| 6,723,116 B2* | 4/2004 | Taheri ........................... 623/1.11 |
| 6,740,115 B2* | 5/2004 | Lombardi et al. ........... 623/1.44 |
| 6,849,088 B2 | 2/2005 | Dehdashtian et al. |
| 6,860,901 B1 | 3/2005 | Baker et al. ................. 623/1.36 |
| 6,878,160 B2 | 4/2005 | Gilligan et al. ............. 623/1.12 |
| 6,962,604 B2 | 11/2005 | Hijlkema |
| 6,974,471 B2 | 12/2005 | Van Schie et al. .......... 623/1.12 |
| 7,147,657 B2 | 12/2006 | Chiang et al. |
| 7,186,263 B2 | 3/2007 | Golds et al. |
| 7,232,459 B2 | 6/2007 | Greenberg et al. .......... 623/1.13 |
| 7,264,632 B2 | 9/2007 | Wright et al. ............... 623/1.12 |
| 7,279,003 B2 | 10/2007 | Berra et al. .................. 623/1.13 |
| 7,318,835 B2 | 1/2008 | Berra ........................... 623/1.12 |
| 7,331,992 B2 | 2/2008 | Randall et al. |
| 7,341,598 B2 | 3/2008 | Davidson et al. ........... 623/1.35 |
| 7,407,509 B2 | 8/2008 | Greenberg et al. |
| 7,473,275 B2 | 1/2009 | Marquez |
| 7,534,258 B2 | 5/2009 | Gomez et al. ............... 623/1.17 |
| 7,615,072 B2 | 11/2009 | Rust et al. |
| 7,722,657 B2 | 5/2010 | Hartley ........................ 623/1.13 |
| 7,758,626 B2 | 7/2010 | Kim et al. |
| 7,766,962 B1 | 8/2010 | Quinn |
| 7,794,492 B2 | 9/2010 | Ishimaru et al. .............. 623/1.2 |
| 7,828,837 B2 | 11/2010 | Khoury |
| 7,887,580 B2 | 2/2011 | Randall et al. |
| 7,927,363 B2 | 4/2011 | Perouse |
| 8,043,354 B2 | 10/2011 | Greenberg et al. |
| 8,128,678 B2 | 3/2012 | Leewood et al. |
| 8,206,427 B1* | 6/2012 | Ryan et al. .................. 623/1.11 |
| 8,292,943 B2 | 10/2012 | Berra et al. .................. 623/1.13 |
| 8,333,799 B2 | 12/2012 | Bales et al. |
| 8,348,994 B2 | 1/2013 | Leopold et al. |
| 8,394,136 B2 | 3/2013 | Hartley et al. |
| 8,425,586 B2 | 4/2013 | Leopold et al. |
| 8,480,725 B2 | 7/2013 | Rasmussen et al. |
| 8,574,284 B2 | 11/2013 | Roeder et al. |
| 8,728,145 B2 | 5/2014 | Chuter et al. |
| 8,740,966 B2 | 6/2014 | Brocker et al. |
| 8,992,593 B2 | 3/2015 | Chuter et al. |
| 9,180,030 B2 | 11/2015 | Brocker et al. |
| 9,220,617 B2 | 12/2015 | Berra |
| 9,226,813 B2 | 1/2016 | Brocker et al. |
| 9,226,814 B2 | 1/2016 | Jensen et al. |
| 9,345,595 B2 | 5/2016 | Brocker et al. |
| 2001/0000188 A1* | 4/2001 | Lenker et al. ............... 623/1.13 |
| 2002/0016627 A1 | 2/2002 | Golds |
| 2002/0022877 A1 | 2/2002 | Mueller et al. |
| 2002/0032487 A1 | 3/2002 | Dua et al. |
| 2002/0143381 A1 | 10/2002 | Gilligan et al. |
| 2002/0177890 A1 | 11/2002 | Lenker |
| 2003/0033002 A1 | 2/2003 | Dehdashtian et al. |
| 2003/0033003 A1 | 2/2003 | Harrison et al. |
| 2003/0050684 A1 | 3/2003 | Abrams et al. |
| 2003/0088305 A1 | 5/2003 | Van Schie et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov et al. |
| 2003/0130720 A1 | 7/2003 | DePalma et al. |
| 2003/0199967 A1 | 10/2003 | Hartley et al. |
| 2004/0002751 A1 | 1/2004 | Gilligan et al. |
| 2004/0054396 A1 | 3/2004 | Hartley et al. |
| 2004/0073289 A1 | 4/2004 | Hartley |
| 2004/0093063 A1 | 5/2004 | Wright et al. |
| 2004/0106978 A1 | 6/2004 | Greenberg et al. |
| 2004/0117003 A1 | 6/2004 | Ouriel et al. |
| 2004/0117004 A1 | 6/2004 | Osborne et al. ............. 623/1.36 |
| 2004/0176833 A1 | 9/2004 | Pavcnik et al. |
| 2004/0215316 A1 | 10/2004 | Smalling |
| 2004/0215319 A1 | 10/2004 | Berra et al. |
| 2004/0254625 A1 | 12/2004 | Stephens et al. |
| 2005/0033406 A1 | 2/2005 | Barnhart et al. |
| 2005/0049674 A1 | 3/2005 | Berra et al. |
| 2005/0075730 A1 | 4/2005 | Myers et al. |
| 2005/0090834 A1 | 4/2005 | Chiang |
| 2005/0102022 A1 | 5/2005 | Solovay et al. |
| 2005/0113905 A1 | 5/2005 | Greenberg et al. |
| 2005/0119722 A1 | 6/2005 | Styrc et al. |
| 2005/0131516 A1 | 6/2005 | Greenhalgh |
| 2005/0154446 A1 | 7/2005 | Phillips et al. .............. 623/1.13 |
| 2005/0159803 A1 | 7/2005 | Lad et al. |
| 2005/0222669 A1 | 10/2005 | Purdy |
| 2005/0222671 A1 | 10/2005 | Schaeffer et al. ........... 623/1.15 |
| 2005/0240257 A1 | 10/2005 | Ishimaru et al. |
| 2005/0240258 A1 | 10/2005 | Bolduc et al. |
| 2005/0273155 A1 | 12/2005 | Bahler et al. |
| 2006/0004433 A1* | 1/2006 | Greenberg et al. .......... 623/1.11 |
| 2006/0004436 A1 | 1/2006 | Amarant et al. |
| 2006/0052860 A1 | 3/2006 | Gomez et al. |
| 2006/0100695 A1 | 5/2006 | Peacock, III et al. ....... 623/1.42 |
| 2006/0161243 A1 | 7/2006 | Fearnot et al. |
| 2006/0184228 A1 | 8/2006 | Khoury |
| 2006/0190070 A1 | 8/2006 | Dieck et al. ................. 623/1.12 |
| 2006/0190075 A1 | 8/2006 | Jordan et al. ................ 623/1.23 |

(56) References Cited

U.S. PATENT DOCUMENTS

| | | |
|---|---|---|
| 2006/0247761 A1 | 11/2006 | Greenberg et al. |
| 2006/0265054 A1 | 11/2006 | Greenhalgh et al. |
| 2006/0267247 A1 | 11/2006 | Anukhin et al. |
| 2007/0027525 A1 | 2/2007 | Ben-Muvhar .............. 623/1.12 |
| 2007/0043425 A1 | 2/2007 | Hartley et al. ............. 623/1.12 |
| 2007/0055345 A1 | 3/2007 | Arbefeuille |
| 2007/0055347 A1 | 3/2007 | Arbefeuille |
| 2007/0067016 A1 | 3/2007 | Jung |
| 2007/0073388 A1 | 3/2007 | Krolik et al. |
| 2007/0100427 A1 | 5/2007 | Perouse |
| 2007/0135889 A1 | 6/2007 | Moore et al. |
| 2007/0142894 A1 | 6/2007 | Moore et al. |
| 2007/0150051 A1 | 6/2007 | Arnault De La Menardiere et al. |
| 2007/0162103 A1* | 7/2007 | Case et al. .................. 623/1.13 |
| 2007/0163668 A1 | 7/2007 | Arbefeuille et al. |
| 2007/0168019 A1 | 7/2007 | Amplatz et al. |
| 2007/0179592 A1 | 8/2007 | Schaeffer |
| 2007/0185560 A1 | 8/2007 | Roeder et al. |
| 2007/0191927 A1 | 8/2007 | Bowe et al. |
| 2007/0203566 A1 | 8/2007 | Arbefeuille et al. ........ 623/1.13 |
| 2007/0208256 A1 | 9/2007 | Marilla |
| 2007/0219620 A1 | 9/2007 | Eells et al. |
| 2007/0219624 A1 | 9/2007 | Brown et al. |
| 2007/0225797 A1 | 9/2007 | Krivoruhko |
| 2007/0233220 A1* | 10/2007 | Greenan .................... 623/1.11 |
| 2007/0233223 A1 | 10/2007 | Styrc et al. |
| 2007/0244547 A1 | 10/2007 | Greenan |
| 2007/0250152 A1 | 10/2007 | Xiao et al. |
| 2007/0282433 A1 | 12/2007 | Limon et al. |
| 2008/0033527 A1 | 2/2008 | Nunez et al. |
| 2008/0039920 A1 | 2/2008 | Peacock et al. |
| 2008/0086190 A1 | 4/2008 | Ta |
| 2008/0109066 A1 | 5/2008 | Quinn |
| 2008/0114441 A1 | 5/2008 | Rust et al. |
| 2008/0114445 A1 | 5/2008 | Melsheimer et al. ....... 623/1.13 |
| 2008/0119943 A1 | 5/2008 | Armstrong et al. ......... 623/23.7 |
| 2008/0140178 A1 | 6/2008 | Rasmussen et al. ........ 623/1.11 |
| 2008/0195191 A1 | 8/2008 | Luo et al. |
| 2008/0269866 A1 | 10/2008 | Hamer et al. |
| 2008/0281399 A1 | 11/2008 | Hartley et al. |
| 2008/0319534 A1 | 12/2008 | Birdsall et al. |
| 2009/0005856 A1 | 1/2009 | Pappas et al. |
| 2009/0043376 A1 | 2/2009 | Hamer et al. |
| 2009/0048663 A1 | 2/2009 | Greenberg |
| 2009/0105809 A1 | 4/2009 | Lee et al. ..................... 623/1.17 |
| 2009/0138072 A1 | 5/2009 | Gendreau .................... 623/1.15 |
| 2009/0149946 A1 | 6/2009 | Dixon |
| 2009/0171437 A1 | 7/2009 | Brocker et al. |
| 2009/0177270 A1 | 7/2009 | Agnew et al. |
| 2009/0306763 A1 | 12/2009 | Roeder et al. |
| 2010/0268318 A1* | 10/2010 | Glynn .......................... 623/1.13 |
| 2010/0331960 A1* | 12/2010 | Clerc ....................... A61F 2/95 |
| | | 623/1.15 |
| 2012/0029624 A1 | 2/2012 | Dierking et al. |
| 2012/0239136 A1 | 9/2012 | Bruzzi |
| 2012/0323307 A1 | 12/2012 | Richter |

FOREIGN PATENT DOCUMENTS

| | | |
|---|---|---|
| EP | 1372530 B1 | 2/2006 |
| EP | 1372534 | 11/2006 |
| EP | 1839624 A1 | 3/2007 |
| EP | 1545396 | 12/2008 |
| JP | 2005-512675 A | 5/2005 |
| JP | 2005-521471 A | 7/2005 |
| JP | 2009-525139 A | 7/2009 |
| KR | 772472 B1 | 6/2007 |
| WO | WO 97/21403 A1 | 6/1997 |
| WO | WO 02/076340 A2 | 10/2002 |
| WO | WO 02/078569 A2 | 10/2002 |
| WO | WO 03/034948 | 5/2003 |
| WO | WO 03/053288 A1 | 7/2003 |
| WO | WO 03/082153 A1 | 10/2003 |
| WO | WO 2004/017867 A1 | 3/2004 |
| WO | WO 2004/017868 | 3/2004 |
| WO | WO 2005/034810 A1 | 4/2005 |
| WO | WO 2005/099628 A1 | 10/2005 |
| WO | WO 2006/028925 A1 | 3/2006 |
| WO | WO 2007/092276 A1 | 8/2007 |
| WO | WO 2007/095283 A1 | 8/2007 |
| WO | WO 2007/098937 A1 | 9/2007 |
| WO | WO 2008/021556 A1 | 2/2008 |
| WO | WO 2008/051543 | 5/2008 |
| WO | 2008066923 A1 | 6/2008 |
| WO | WO 2009/020653 A1 | 2/2009 |
| WO | WO 2010/024879 A1 | 3/2010 |
| WO | 2010062355 A1 | 6/2010 |

OTHER PUBLICATIONS

PCT/US2010/056673 Written Opinion, MED Institute, Inc, May 6, 2011.
Office Action received for U.S. Appl. No. 12/609,553, dated Dec. 20, 2010 (10 pages).
Office Action received for U.S. Appl. No. 12/609,553, dated Apr. 4, 2011 (11 pages).
Advisory Action received for U.S. Appl. No. 12/609,553, dated Jun. 3, 2011 (3 pages).
Office Action received for U.S. Appl. No. 12/609,553, dated Oct. 11, 2011 (15 pages).
Office Action received for related U.S. Appl. No. 12/945,097, dated Feb. 29, 2012 (14 pages).
Office Action received for U.S. Appl. No. 12/609,553, dated Mar. 9, 2012 (16 pages).
Advisory Action received for U.S. Appl. No. 12/609,553, dated May 24, 2012 (5 pages).
Office Action received for related U.S. Appl. No. 12/946,233, dated Aug. 16, 2012 (18 pages).
Notice of Panel Decision received for U.S. Appl. No. 12/609,553, dated Dec. 26, 2012 (2 pages).
Office Action received for related U.S. Appl. No. 12/945,097, dated Dec. 26, 2012 (11 pages).
Patent Examination Report No. 1 for corresponding Patent App. No. AU 2010322201, dated Jun. 25, 2013, (4 pages).
Patent Examination Report No. 2 for corresponding Patent App. No. AU 2010322201, dated Aug. 7, 2013, (6 pages).
Communication for corresponding Patent App. No. EP 20779432.3, dated May 4, 2012, (4 pages).
Search Report under Section 17 for corresponding Patent App. No. GB 0920327.4, dated Feb. 9, 2011, (1 page).
Translation of Office Action of corresponding Patent App. No. JP 2012-539958, dated Jun. 3, 2014, (2 pages).
International Search Report for corresponding Patent App. No. PCT/US2010/056673, dated May 11, 2011, (16 pages).
International Preliminary Report on Patentability for corresponding Patent App. No. PCT/US2010/056673, dated May 22, 2012, (9 pages).
Amendment and Reply to Office Action filed in related U.S. Appl. No. 12/946,233, dated Jan. 16, 2013 (9 pages).
Final Office Action mailed in related U.S. Appl. No. 12/946,233, dated May 7, 2013 (23 pages).
Amendment Accompanying an RCE filed in related U.S. Appl. No. 12/946,233, dated Sep. 9, 2013 (9 pages).
Office Action mailed in related U.S. Appl. No. 12/946,233, dated Apr. 25, 2014 (13 pages).
Response to Non-Final Office Action filed in related application U.S. Appl. No. 12/946,233, dated Jul. 25, 2014 (8 pages).
Office Action mailed in related application U.S. Appl. No. 12/946,233, dated Aug. 29, 2014 (13 pages).
Response to Non-Final and Interview Summary filed in related application U.S. Appl. No. 12/946,233, dated Jan. 23, 2015 (8 pages).
Final Office Action received for related U.S. Appl. No. 12/946,233, dated Feb. 24, 2015 (13 pages).
After Final Pilot Response to Office Action filed in related U.S. Appl. No. 12/946,233, dated May 26, 2015 (9 pages).

(56) References Cited

OTHER PUBLICATIONS

Amendment and Reply filed in related U.S. Appl. No. 12/945,097, dated Aug. 28, 2012 (8 pages).
Final Office Action mailed in related application U.S. Appl. No. 12/945,097, dated Dec. 26, 2012 (11 pages).
Amendment Accompanying an RCE filed in related U.S. Appl. No. 12/945,097, dated Apr. 26, 2013 (8 pages).
Supplement Amendment filed in related U.S. Appl. No. 12/945,097, dated Jul. 24, 2013 (7 pages).
Corrected Supplement Amendment filed in related U.S. Appl. No. 12/945,097, dated Sep. 18, 2014 (6 pages).
Office Action received for related U.S. Appl. No. 12/945,097, dated Oct. 6, 2014 (17 pages).
Response to Non-Final Office Action filed in related U.S. Appl. No. 12/945,097, dated Jan. 30, 2015 (14 pages).
Amendment and Response filed in related U.S. Appl. No. 12/609,553, dated Mar. 9, 2011 (8 pages).
Amendment and Response filed in related U.S. Appl. No. 12/609,553, dated May 25, 2011 (8 pages).
Amendment and Response filed in related U.S. Appl. No. 12/609,553, dated Jan. 11, 2012 (15 pages).
Final Office Action received for U.S. Appl. No. 12/609,553, dated May 9, 2012 (5 pages).
Pre-Appeal Brief Request for Review filed for related U.S. Appl. No. 12/609,553, dated Sep. 7, 2012 (6 pages).
Notice of Allowance received for related U.S. Appl. No. 12/609,553, dated Mar. 13, 2013 (10 pages).
PCT Partial International Search Report for PCT/US2010/056673, date of mailed Mar. 2, 2011 (3 pages).
First Examination Report for Australian Patent Application No. 2008341104 issued Oct. 16, 2012, 3 pages.
Second Examination Report for Australian Patent Application No. 2008341104 issued Jul. 9, 2013, 3 pages.
Examination Report No. 1 for AU 2014200561 dated Apr. 27, 2015, 4 pages.
Extended European Search Report for EP12275202 dated Apr. 9, 2013, 8 pages.
Examination Report for European Patent Application Serial No. 08 864 911.6 dated Aug. 8, 2012, 4 pages.
Examination Report for European Patent Application Serial No. 08 864 911.6 dated Jan. 9, 2013, 4 pages.
Examination Report for European Patent Application Serial No. 08 864 911.6 dated Nov. 10, 2014, 3 pages.
European Search Report for European Patent Application 11174880, dated Jul. 23, 2012, 6 pages.
Partial Search Report for European Patent Application Serial No. 11 174 880.2 dated Aug. 8, 2012, 5 pages.
Extended Search Report for European Patent Application Serial No. 11 174 880.2 dated Feb. 8, 2013, 9 pages.
Examination Report for European Patent Application Serial No. 11 174 880.2 dated Sep. 2, 2014, 4 pages.
Combined Search and Examination Report for Great Britain Patent Application Serial No. 0920235.9 dated Mar. 16, 2010, 3 pages.
Examination Report for Great Britain Patent Application Serial No. 0920235.9 dated Jun. 14, 2010, 2 pages.
Office Action for corresponding JP 2014-203749 and translation, mailed Sep. 29, 2015, 7 pages.
Office Action Notice of Grounds of Rejection for Japanese Patent Application No. 2010-540640 mailed Nov. 20, 2012, 8 pages including English translation.
Office Action Notice of Grounds of Rejection for Japanese Patent Application Serial No. 2010-540640 dated Nov. 5, 2013, 7 pages, including English Translation.
International Search Report and Written Opinion for PCT/US2008/013738 dated Feb. 19, 2009, 7 pages.
International Preliminary Report on Patentability for PCT/US2008/013738 dated Dec. 11, 2009, 5 pages.
International Search Report for PCT/US2011/056365 dated Jul. 18, 2012, 5 pages.

Written Opinion for PCT/US2011/056365 dated Apr. 14, 2013, 6 pages.
International Preliminary Report on Patentability for PCT/US2011/056365 dated Apr. 16, 2013, 7 pages.
Non-Final Office Action for U.S. Appl. No. 12/332,904 dated Oct. 4, 2010, 8 pages.
Final Office Action for U.S. Appl. No. 12/332,904 dated May 9, 2011, 11 pages.
Non-Final Office Action for U.S. Appl. No. 12/332,904 dated Nov. 18, 2011, 12 pages.
Final Office Action for U.S. Appl. No. 12/332,904 dated Jan. 3, 2013, 5 pages.
Non-Final Office Action for U.S. Appl. No. 12/332,904 dated Jan. 14, 2015, 5 pages.
Notice of Allowance for U.S. Appl. No. 12/332,904 dated Jul. 6, 2015, 8 pages.
Non-Final Office Action for U.S. Appl. No. 12/472,082 dated Oct. 4, 2010, 8 pages.
Non-Final Office Action for U.S. Appl. No. 12/472,082 dated Jun. 2, 2011, 12 pages.
Non-Final Office Action for U.S. Appl. No. 14/472,082 dated Dec. 2, 2011, 11 pages.
Final Office Action for U.S. Appl. No. 12/472,082 dated Sep. 13, 2012, 14 pages.
Notice of Allowance for U.S. Appl. No. 12/472,082 dated Jun. 21, 2013, 10 pages.
Notice of Allowance for U.S. Appl. No. 12/472,082 dated Aug. 14, 2013, 4 pages.
Non-Final Office Action for U.S. Appl. No. 12/622,351 dated Oct. 6, 2010, 10 pages.
Final Office Action for U.S. Appl. No. 12/622,351 dated Jun. 10, 2011, 12 pages.
Non-Final Office Action for U.S. Appl. No. 12/622,351 dated Dec. 1, 2011, 13 pages.
Non-Final Office Action for U.S. Appl. No. 12/622,351 dated Jun. 27, 2012, 25 pages.
Final Office Action for U.S. Appl. No. 12/622,351 dated Apr. 3, 2013, 28 pages.
Notice of Allowance for U.S. Appl. No. 12/622,351 dated Sep. 4, 2013, 8 pages.
Notice of Allowance for U.S. Appl. No. 12/622,351 dated Jan. 21, 2014, 7 pages.
Office Action Restriction Requirement for U.S. Appl. No. 12/841,807 dated Feb. 24, 2012, 9 pages.
Non-Final Office Action for U.S. Appl. No. 12/841,807 dated Jun. 7, 2012, 9 pages.
Final Office Action for U.S. Appl. No. 12/841,807 dated Jan. 11, 2013, 9 pages.
Non-Final Office Action for U.S. Appl. No. 12/841,807 dated Jul. 31, 2014, 10 pages.
Notice of Allowance for U.S. Appl. No. 12/841,807 dated Nov. 24, 2014, 7 pages.
Non-Final Office Action for U.S. Appl. No. 12/904,452 dated May 15, 2012, 11 pages.
Final Office Action for U.S. Appl. No. 12/904,452 dated Dec. 19, 2012, 11 pages.
Final Office Action for U.S. Appl. No. 12/904,452 dated May 1, 2014, 11 pages.
Advisory Action for U.S. Appl. No. 12/904,452 dated Jun. 13, 2014, 2 pages.
Notice of Allowance for U.S. Appl. No. 12/904,452 dated Mar. 9, 2015, 5 pages.
Notice of Allowance for U.S. Appl. No. 12/904,452 dated Aug. 27, 2015, 5 pages.
Final Office Action for U.S. Appl. No. 12/945,097 dated Jul. 2, 2015, 10 pages.
Advisory Action for U.S. Appl. No. 12/945,097 dated Dec. 30, 2015, 3 pages.
Non-Final Office Action for U.S. Appl. No. 12/945,097 dated Sep. 8, 2016, 10 pages.
Notice of Allowance for U.S. Appl. No. 12/946,233 dated Jun. 8, 2015, 11 pages.

(56) References Cited

OTHER PUBLICATIONS

Non-Final Office Action for U.S. Appl. No. 13/335,142 dated Feb. 14, 2013, 16 pages.
Notice of Allowance for U.S. Appl. No. 13/335,142 dated Sep. 23, 2013, 11 pages.
Notice of Allowance for U.S. Appl. No. 13/335,142 dated Jan. 16, 2014, 7 pages.
Non-Final Office Action for U.S. Appl. No. 14/293,286 dated Aug. 5, 2015, 17 pages.
Notice of Allowance for U.S. Appl. No. 14/293,286 dated Jan. 15, 2016, 9 pages.
Non-Final Office Action for U.S. Appl. No. 14/876,429 dated Jun. 30, 2016, 5 pages.
Non-Final Office Action for U.S. Appl. No. 14/952,498 dated Aug. 11, 2016, 8 pages.

* cited by examiner

STENT GRAFT AND INTRODUCER ASSEMBLY

TECHNICAL FIELD

The present invention relates to a stent graft designed to treat Type-A dissections, that is dissections occurring close to the heart in the ascending aorta. The present invention also relates to an introducer assembly for the deployment of a stent graft into the ascending aorta to treat Type-A dissections. The stent graft and introducer assembly disclosed herein can also be used to treat aortic ruptures, transactions, coronary dissections, valve ruptures, cardiac tamponades, distal malperfusions and other similar defects.

RELATED APPLICATIONS

This application claims priority to Great Britain Patent Application No. GB0920327.4, filed Nov. 19, 2009, and is further related to U.S. Provisional Application Ser. No. 61/262,839, filed Nov. 19, 2009, U.S. patent application Ser. No. 12/622,351, filed Nov. 19, 2009, now U.S. Pat. No. 8,740,966, issued Jun. 3, 2014, and is further related to co-pending U.S. application Ser. No. 12/946,233, filed Nov. 15, 2010, co-pending U.S. application Ser. No. 12/945,097, filed Nov. 10, 2010, and Great Britain Patent Application No. GB0920235.9, filed Nov. 18, 2009, all of which are incorporated by reference in their entirety.

BACKGROUND ART

Dissections occur when the wall of a lumen tears, creating a secondary or false lumen. Blood can flow into this false lumen, generally causing the vessel to balloon outwardly as a result of the weaker lumen wall. If the dissection is left untreated, there is the risk of rupture of the lumen, with severe consequences to the patient. Dissections can be treated by open surgery, involving closing the tear by suturing and/or strengthening of the lumen wall, again often by suturing. Open surgery procedures should, however, preferably avoided, particularly to the thoracic region, in light of the trauma caused to the patient. For this purpose, some endoluminal treatments have been developed in which the dissection is treated by means of a stent or stent graft placed against the damaged portion of the vessel wall. The stent or stent graft acts to press together the two parts of the lumen wall so as to close off the false lumen. It have been found that if the false lumen can be closed, the lumen wall often repairs itself. A stent graft can usefully be placed at the point of the tear, so as to close off the blood supply to the false lumen. This removes the blood pressure in the false lumen and thus allows the two parts of the lumen wall to come into contact one another and thus to heal in time.

The use of stents and stent grafts to treat dissections has been restricted to lumen locations and zones which are free of complications, such as branch vessels, complex lumen geometries and so on, particularly in light of the difficulties in placing the stent and stent grafts accurately in the lumen. As a result of the particular complexities of Type-A dissections, that is dissections in the ascending aorta, stents or stent grafts have not been used. At this location, there is only a short length of aorta which is free of side branches critical to the health of the patient. The geometry of the lumen, that is beyond the aortic arch, also causes positioning difficulties.

More particularly, a Type-A thoracic aorta dissection (TAD-A) is a condition in which the intimal layer of the ascending thoracic aorta develops a tear, allowing blood to flow into the layers of the aortic wall, causing the development of medial or subintimal hematoma. TAD-A is associated with a very high mortality rate of around 1 to 2% per hour for the first 48 hours. Currently, the only option for treatment of TAD-As is open surgical repair which includes opening the chest cavity, clamping the aorta and sewing a vascular prosthesis in place. Operative mortality rate for TAD-A is significant at approximately 10%.

The ability to treat a TAD-A quickly is imperative but current procedures are lengthy, invasive and associated with high morbidity and mortality. The ability to treat TAD-As through endovascular procedures would represent a significant step forward and reduction in mortality rates. However, the ascending aortic arch is complex by reason of the coronary arteries and brachiocephalic artery and that any obstruction of these can lead to patient demise. As a result of this, the treatment of Type-A dissections and other vascular defects in the ascending aorta still remains restricted to open surgical procedures.

DISCLOSURE OF THE INVENTION

The present invention seeks to provide a stent graft assembly for the treatment of Type-A dissections and to an introducer assembly able to place a stent graft in the ascending aorta for the treatment of Type-A dissections. The stent graft and introducer assembly disclosed herein can also be used to treat aortic ruptures, transactions, coronary dissections, valve ruptures, cardiac tamponades, distal malperfusions and other similar defects.

According to an aspect of the present invention, there is provided a stent graft for treatment of defects in the ascending aorta including a tubular portion of graft material provided with proximal and distal ends, a plurality of stent rings attached to the graft tube, at least one bare stent extending from the proximal end of the graft tube and designed to flare outwardly relative to the graft tube so as to engage in use the aortic sinus of a patient.

This arrangement of stent graft has the advantage of maintaining the stent graft in position and preventing its migration. This can be particularly useful given the disadvantages of using barbs in this part of a patient's anatomy, and such that the preferred embodiment of stent graft is provided with no barbs at all and at least no barbs in its proximal end. Therefore, this structure can provide a medical device able to treat vascular defects in the ascending aorta.

In practice, the bare stent is designed and arranged to be located in the bulbous part of the aorta by the aortic arteries and by the heart itself. This bare stent can thus assist in holding the stent graft in position in the lumen.

In the preferred embodiment, there are provided bare stents at both the proximal and distal ends of the graft tube. The bare stent at the distal end of the graft tube can assist in the anchoring of the stent graft in the ascending aorta, to prevent migration of this over the brachiocephalic artery. The distal bare stent preferably flares outwardly relative to the graft tubing The or each bare stent is preferably formed of an undulating stent structure, to provide a series of fingers arranged circumferentially around the graft tubing and having curved ends or apices. This design of bare stent avoids sharp points to the stent structure and therefore minimizes trauma to the vessel walls.

In the preferred embodiment, the graft tubing is in the region of 65 mm in length and the or each bare stent extends from the graft tubing by around 10 mm.

According to another aspect of the present invention, there is provided a method of treating a vascular defect in the ascending aorta of a patient including the steps of locating in the ascending aorta a stent graft provided with a tubular portion of graft material provided with proximal and distal ends, a plurality of stent rings attached to the graft tube, at least one bare stent extending from the proximal end of the graft tube and designed to flare outwardly relative to the graft tube, said positioning locating the bare stent in the aortic sinus of a patient so as to anchor the stent graft in position.

According to another aspect of the present invention, there is provided a stent graft including a tubular portion of graft material provided with proximal and distal ends, a plurality of stent rings attached to the graft tube, and at least first and second diameter restraining devices, the first diameter restraining device being located at or proximate the proximal end of the graft tube, the or at least one second diameter restraining device being located in an intermediate position along the graft tube.

The diameter restraining devices provide for the graft tube and thus the stent graft to be deployed at an initial, partially expanded state in which the graft tube can expand radially outwardly in those zones thereof not restrained by the restraining devices, with the central portion of the graft tube being kept in a constrained configuration. The keeps the stent graft in a configuration in which it can be repositioned within the patient's lumen prior to full deployment thereof. Once the stent graft is in the correct and precise position, the restraining devices can be released to deploy the stent graft fully in the lumen.

Such repositioning is extremely important in being able to treat Type-A dissections by means of stent grafts, in that the position of the stent graft can be adjusted very precisely, ensuring that the graft tube does not block either the coronary arteries or the brachiocephalic artery.

In the preferred embodiment, the restraining devices are diameter reducing loops disposed circumferentially around the graft tube. Such loops can be used in combination with trigger wires to restraining the diameter of the stent graft at the location of the loops.

Preferably, there are provided at least two intermediate diameter restraining devices, operable to restrain proximal and distal ends of a stent located on the graft tube or a plurality of stents positioned in an intermediate position along the graft tube.

The diameter restraining devices can thus allow the proximal and distal zones of the graft tubing to expand outwardly in a first deployment stage, generally on withdrawal of the outer sheath of the introducer assembly. This provides a first deployed condition of the stent graft in which portions of the stent graft may contact the lumen walls yet still be movable.

In the preferred embodiment, the stent graft includes at least one bare stent extending from a proximal end of the graft tube. Such a bare stent can have the function of maintaining the stent graft in position and preventing its migration. This can be particularly useful given the disadvantages of using barbs in this part of a patient's anatomy.

Advantageously, the bare stent is designed to flare outwardly relative to the graft tubing. In practice, the bare stent is designed and arranged to be located in the bulbous part of the aorta by the aortic arteries and by the heart itself. This bare stent can thus assist in holding the stent graft in position in the lumen.

In the preferred embodiment, there are provided bare stents at both the proximal and distal ends of the graft tube.

The bare stent at the distal end of the graft tube can assist in the anchoring of the stent graft in the ascending aorta, to prevent migration of this over the brachiocephalic artery. The distal bare stent preferably flares outwardly relative to the graft tubing The or each bare stent is preferably formed of an undulating stent structure, to provide a series of fingers arranged circumferentially around the graft tubing and having curved ends or apices. This design of bare stent avoids sharp points to the stent structure and therefore minimizes trauma to the vessel walls.

Advantageously the graft tubing is in the region of 65 mm in length and the or each bare stent extends from the graft tubing by around 10 mm.

In the preferred embodiment, the stent graft is provided with a stent section extending from the distal end of the graft tubing. In use, the stent section extends across the brachiocephalic, left common cartoid and left subclavian arteries. Being of open construction, the stent does not impinge upon the flow of blood into these arteries while providing support to the graft section against its migration. The stent section could be integral with the graft section, that is of unitary construction, but in the preferred embodiment is formed as a separate component deployable after deployment of the stent graft section.

According to another aspect of the present invention, there is provided an introducer assembly for deploying a stent graft as specified herein, the introducer assembly including a carrier for carrying the stent graft, an outer sheath movable from a position covering the carrier to a withdrawn position exposing the carrier; the introducer assembly including a plurality of restraining elements for maintaining the restraining devices of the stent graft in a radially compressed configuration after withdrawal of the sheath.

The restraining elements are thus able to keep the stent graft attached to an partially deployed on the introducer for final positioning before complete deployment.

Advantageously the restraining elements include one or more trigger wires. In one embodiment, the trigger wires are arranged to restrain the proximal bare stent as well as the restraining devices and to release these from a proximal most position to a distal most position upon withdrawal of the restraining wires. The restraining wires may also hold the distal end of the stent graft, for instance the distal bare stent where this is provided. The restraining wires can thus allow for staged deployment from the proximal-most part of the stent graft to its distal end.

In another embodiment, there may be provided a plurality of sets of trigger wires for releasing the stent graft in a different sequence than from one end of the graft tube to the other. For instance, one set of trigger wires may be arranged to release the distal end of the stent graft first and one or more other sets of trigger wires arranged to release other portions of the stent graft, for instance its proximal end and/or the central portion whether together or independently of one another.

Advantageously, the introducer is provided with a pliable dilator tip able to be passed through a patient's heart valve during the deployment procedure.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
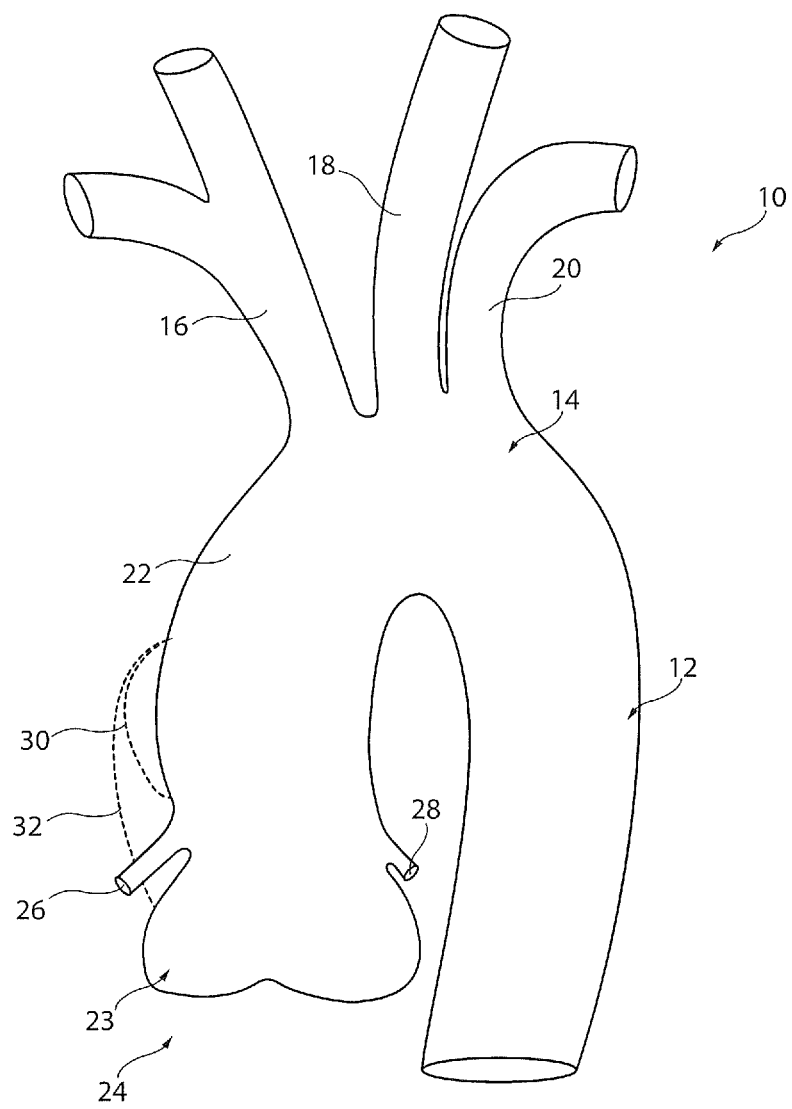
FIG. 1 shows an example of a patient's aorta.

Referring to FIG. 1, there is shown an example of a patient's aorta 10. The aorta includes a descending aorta portion 12 leading to the aortic arch 14 from which extend the brachiocephalic artery 16, the left common cartoid artery 18 and the left subclavian artery 20. Beyond the aortic arch 14 there is the ascending aorta 22 leading to the heart opening 24, just before which the coronary arteries 26, 28 branch off.

Until now dissections and aneurisms could be treated only in the descending aorta 12 by way of stents and stent grafts, in light of the difficulty of positioning such devices accurately in the aortic arch 14 or the ascending aorta 22 and as a result of the numerous arterial branches leading off these parts of the aorta. Particular difficulties arise with dissections or aneurisms occurring at the mouth of the heart and proximate or bridging the coronary arteries, as shown for instance in the dotted outlines in FIG. 1. Outline 30 shows in schematic form the effect of a dissection just downstream of the coronary arteries 26, 28, while line 32 shows the outline of a dissection starting upstream of the coronary arteries 26, 28.

In practice, the length of lumen of the ascending aorta 22 free of branch arteries is no more than around 50 to 60 mm, meaning that any medical device to be located in this area must be positioned very accurately in order not to run the risk of blocking any of the branching arteries or causing trauma to the tissue of the lumen walls.

Figure 2:
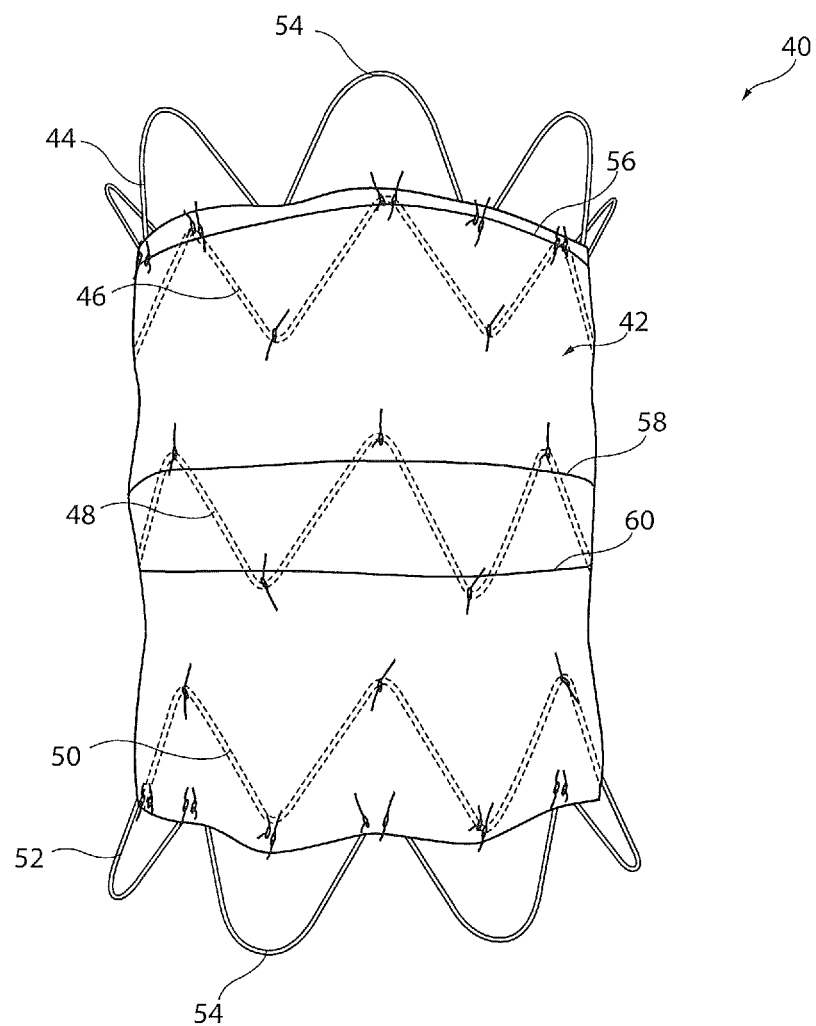
FIG. 2 is a side elevational view of a preferred embodiment of stent graft.

Referring to FIG. 2, there is shown an embodiment of a stent graft 40 designed to be fitted into the ascending aorta 22 to treat a Type-A dissection 30, 32. Although the stent graft and introducer assembly disclosed herein focus upon the treatment of Type-A dissections, they can also be used to treat aortic ruptures, transactions, coronary dissections, valve ruptures, cardiac tamponades, distal malperfusions, aneurysms and other similar defects.

The stent graft 40 includes a tube 42 of graft material, which may be any of the currently available graft materials or other materials contemplated in the art. The graft tube 42 preferably has a length of around 50-70 mm, in the preferred embodiment around 65 mm, and a diameter in the range from 28 mm to 46 mm. These dimensions do, of course, depend upon the size of a patient's ascending aorta 22 and the distance between the coronary arteries 26, 28 and the brachiocephalic artery 16.

In this embodiment, the stent graft 40 is provided with five stent rings 44, 46, 48, 50 and 52, two of which, that is stents 44 and 52, are bare stents which extend beyond the extremities of the graft tube 42. The other three stent rings 46-50 are, in this embodiment, disposed on the inside of the graft tube 42 and are spaced along its length, such that the rings 46 and 50 are proximate the ends of the graft tube while the stent ring 48 is approximately at its centre.

The bare stents 44 and 52 have, in the preferred embodiment, rounded apices 54 to minimize the risk of damage to the vessel walls. Although the preferred embodiment has two bare stents, a proximal stent 44 and a distal stent 52, the distal stent 52 may be omitted. It will be seen from the drawings that at least the proximal bare stent 44 flares outwardly, that is radially beyond the graft tube 42. The distal bare stent 52 may flare in similar manner.

The internal stent rings 46, 48, 50 may be conventional zigzag stent rings with pointed apices, although could have rounded apices as the bare stents 44 and 52, or any other suitable stent ring design.

In the embodiment shown, the stent rings 44, 46, 48, 50, 52 are sutured to the graft tube in conventional manner although they could be secured to the graft tube 42 by any other suitable means.

Fitted to the graft tube 42 are a plurality of diameter restraining devices, in this embodiment diameter reducing suture loops 56, 58, 60. The proximal suture loop 56 extends around the proximal end of the graft tube 42 and in this embodiment feeds into and out of the graft material to provide a plurality of portions of thread substantially evenly radially spaced on the inside of the graft tube, for tying to the carrier of an introducer, as described in further detail below. The diameter reducing loop 56 is usefully threaded into the inside of the graft tube at the apices of the stent 44, such that the stent structure provides support for the loop 56.

The intermediate diameter reducing loops 58, 60 are, in this embodiment, provided at either end of the middle stent ring 48 and again feed into the inside of the graft tube 42 at the apices of the stent ring 48.

In this embodiment, the distal end of the stent graft 40 is not provided with any diameter reducing loops. In other embodiments, a further diameter reducing loop may be provided at this end of the graft tube 42.

It will be appreciated that there could be provided a single intermediate diameter reducing loop 58, 60 or more than two, in dependence upon the design of the stent ring 48 and the number of stent rings provided in the central portion of the graft tube 42. It is preferred in this embodiment to have two intermediate diameter reducing loops 58, 60 in order to constrain the central stent ring 48 at both of its ends to a carrier of the introducer, as shown in further detail below.

Figure 3:
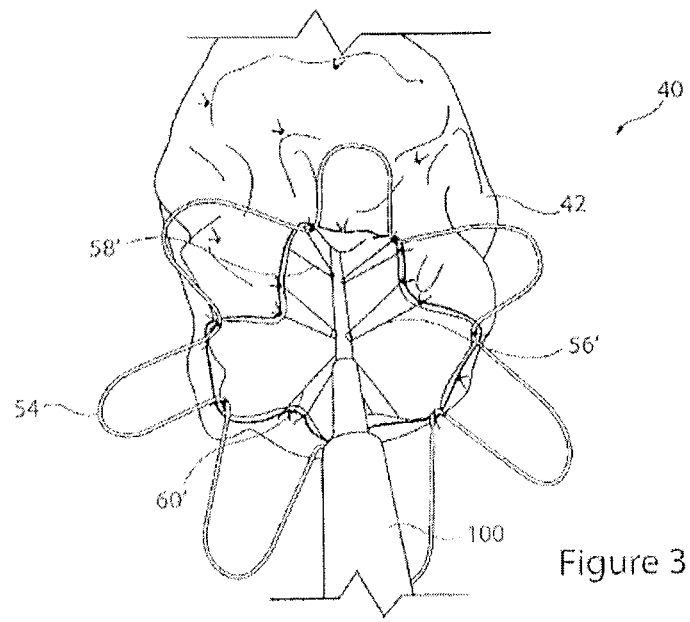
FIG. 3 is a view from the front of the stent graft of FIG. 2 showing the diameter constraining mechanism.

Referring now to FIG. 3, there is shown the stent graft 40 constrained on an introducer (the latter being described in further detail below), with the diameter reducing loops 56, 58, 60 pulled by their portions which extend into the graft tubing 42 towards the centre-point of the stent graft (in practice towards the carrier cannula as shown in the Figure). The number of constraining points on the graft tube 42 will depend upon the number of portions of loop 56, 58, 60 extending into the graft tube. In this example, there are three constraining points 56', 58', 60' per loop, as will be apparent from FIG. 3.

Figure 4:
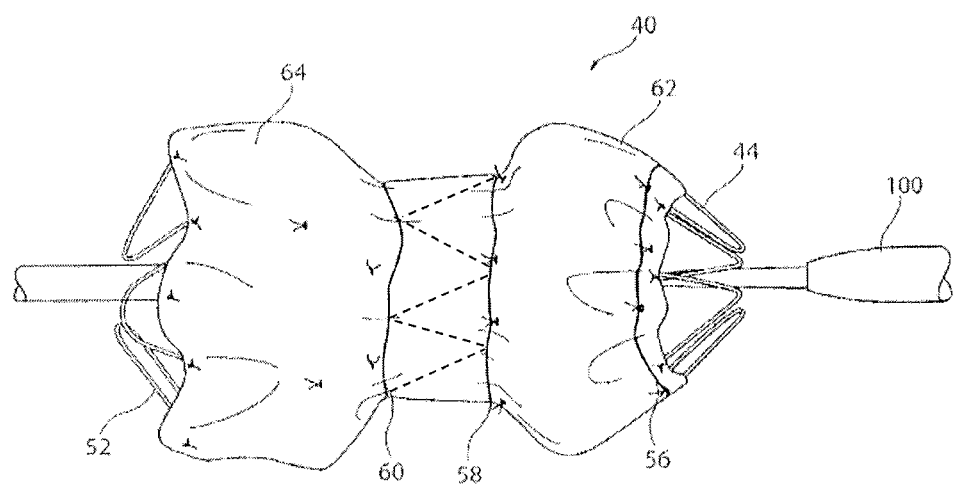
FIG. 4 is a side elevational view of the stent graft of FIG. 2 in a partially constrained configuration.

Referring now to FIG. 4, there is shown a side elevational view of the stent graft 40 fitted onto the distal end of an introducer 100 and in a condition in which the stent graft 40 has been partially deployed but remains constrained on the introducer 100. In this configuration, the diameter reducing loops 58, 60 constrain the radial expansion of the stent graft 40 until these are released from the introducer 100, as described below. Thus, in this configuration, the stent graft 42 produces two bulbous regions 62, 64 either side of its centre portion and within the ends of the graft tube. In this state, the stent graft 40, which could be described as being in a partially deployed configuration, can be repositioned in a patient's lumen thus to enable very accurate positioning of the stent graft in the ascending aorta 22.

FIG. 4 also shows the ends of the bare stents 44, 52 constrained to the carrier of the introducer.

Figure 5:
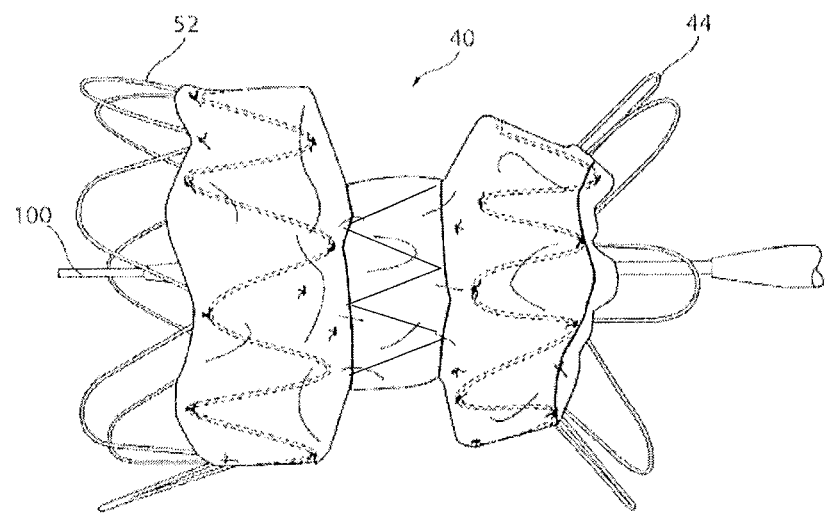
FIG. 5 is a side elevational view of the stent graft of FIG. 2 in a partially constrained configuration and with its distal end and the proximal bare stent released.

Referring now to FIG. 5, the stent graft 40 is shown in a configuration in which the bare stents have been released from the carrier and thus are able to expand radially outwardly, in practice towards the lumen walls of a patient. In the view of FIG. 5, both bare stents 44, 52 have been released, although in some embodiments the distal bare stent 52 may remain constrained until the remainder of the stent graft 40 has been deployed, that is being the last element of the stent graft which is released to expand. This is described in further detail below.

Figure 6:
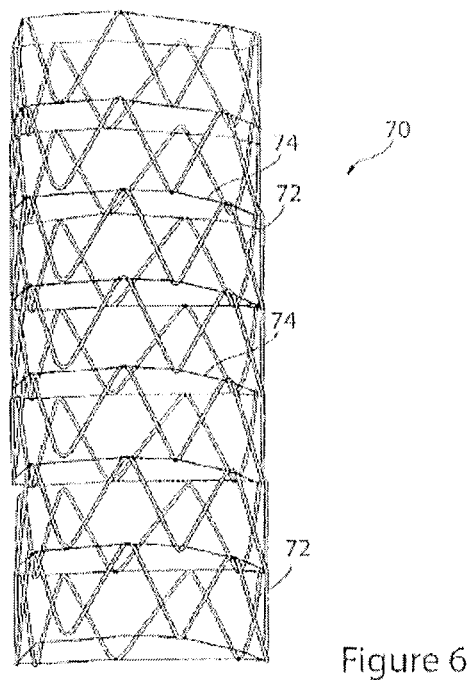
FIG. 6 is a side elevational view of an embodiment of stent for use in fixing the stent graft of FIG. 2 in position.

Referring now to FIG. 6, there is shown an embodiment of distal stent 70 for use with the stent graft 40. The stent 70 can take any desired form although in this embodiment is formed of a plurality of zigzag stent rings 72 tied together by a plurality of threads 74. This type of stent is longitudinally very flexible yet can provide a good radial expansion force against the lumen walls.

Figure 7:
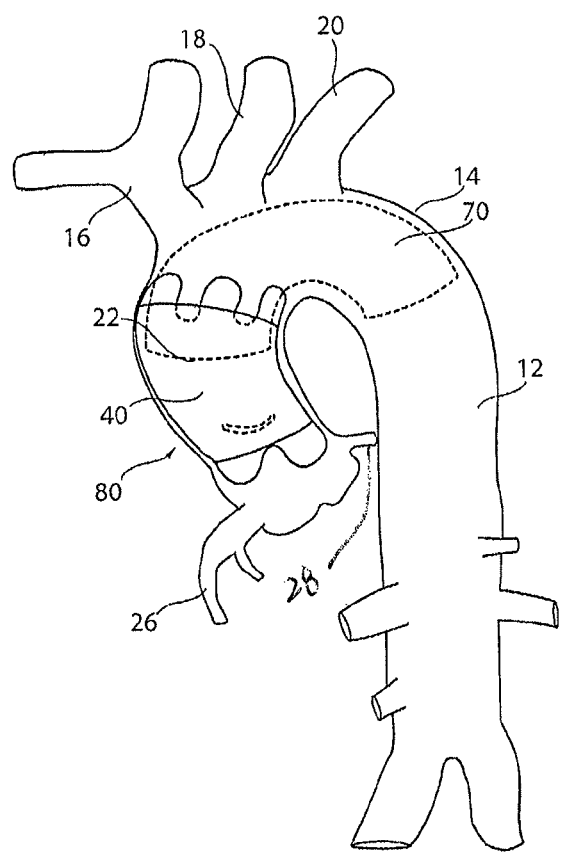
FIG. 7 is a schematic diagram of the stent graft of FIG. 2 and the stent of FIG. 6 in situ in the aorta of a patient.

FIG. 7 shows the stent graft 40 and stent 70 assembly fitted to a patient's aorta, specifically with the stent graft 40 located in the ascending aorta 22 and the stent 70 extending over the arterial branches 16, 18, 20.

The proximal bare stent 44 locates into the bulbous region 23 of the aorta just by the heart opening 24 and across the coronary arteries 26, 28. Given its flaring configuration, the bare stent opens out into the bulbous region 23 and acts to assist in holding the stent graft 40 in position. The graft section 42 extends over the entry point or tear 80 forming the opening of the dissection, and down close to the brachiocephalic artery 16.

The distal stent 70 is positioned such that its proximal end fits inside and against the stent graft 40 and extends across the branch arteries 16, 18, 20. The stent 70 acts to press the distal end of the stent graft 40 against the lumen walls and to maintain the position of the stent graft 40, thereby to prevent its migration.

In some embodiments the stent graft 40 and stent 70 could be formed integrally, that is as a unitary structure. It is preferred, however, that the two are separate components.

Figure 8:
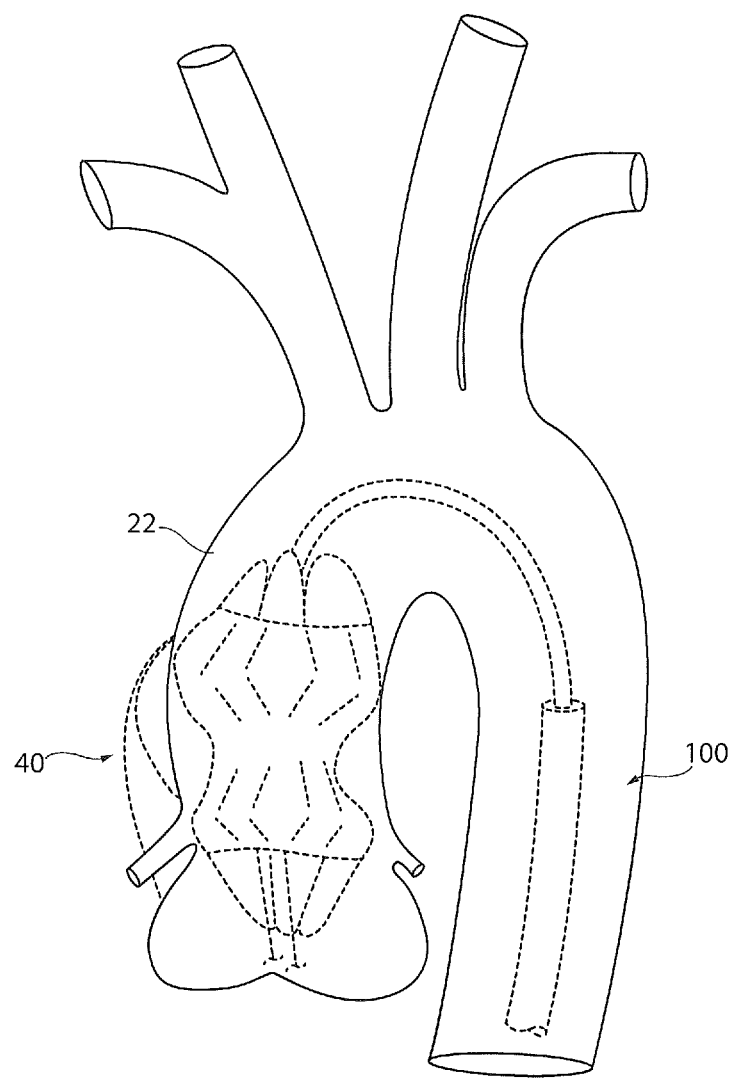
FIG. 8 is a schematic diagram of the stent graft of FIG. 2 in a partly deployed configuration in the aorta of a patient.

FIG. 8 shows the stent graft 40 in position in the ascending aorta in a partially deployed state and still attached to, and partially constrained to, the introducer 100. As can be seen, the stent graft 40 is able to expand towards the walls of the lumen but is still able to be moved backward and forward as necessary along the lumen to ensure its correct positioning before it is completely released from the introducer.

Although FIGS. 2 to 8 focus on an embodiment of stent graft provided with a plurality of diameter constricting devices 56, 58, 60, these are not necessary in all embodiments of the invention. In particular, the stent graft could be provided as a structure with a bare stent 44 at its proximal end and a plurality of stents coupled to the graft tube 42. The loops 56, 58, 60 and the distal bare stent 52 need not be used.

In this embodiment, the bare stent 44 flares outwardly, in use to engage the concavity of the aortic sinus 23 and thus to act as an anchoring element to ensure that the stent graft 40 remains in place beyond the coronary arteries 26, 28 and does not migrate to obstruct the brachiocephalic artery 16. The bare stent 44 preferably extends out of the graft tube by a predetermined distance to provide adequate anchoring to the aortic sinus 23 and may, for instance, extend by around 10 mm for an adult. This design of bare stent also acts to resist any forces acting to push the device proximally as the bare stents will engage the aortic root tissue (the apices of the stent will be driven into the concave aortic root and will prevent proximal device motion).

The stent graft 40 also preferably includes the distal bare stent 52, which has the function of anchoring the stent graft 40 against upstream migration, thereby preventing migration to the aortic valves. The bare stents 44, 52 thus enable the stent graft not to have any barbs, which can cause damage to the vessel walls.

The amount of bare stent which is exposed beyond the graft tube 42 can be controlled by the position of the sutures holding the bare stent.

Although the embodiment of stent graft shown has the stents 46, 48 and 50 located inside the graft tube 42, in the preferred embodiment, the middle stent 48 is located on the outside of the graft tube 42. In this manner, the stent 48 acts as a body stent providing longitudinal and circumferential stability to the device ensuring that the device confirms to the vasculature and does not buckle when deployed in angulated and/or tortuous anatomies. The stent 46 and 50 are sealing stents which ensure good sealing of the stent graft 40 to the vessel walls.

This embodiment of stent graft may also be used with a distal stent of the type shown in FIG. 6, which may be a separate component or integral with the stent graft 40.

The graft tube, as with the embodiment of FIGS. 2 to 8, can have a length of around 50 to 70 mm for an adult and preferably a length of around 65 mm. It can have similar diameters as the embodiment of FIGS. 2 to 8.

In all embodiments, the stents are preferably formed from shape memory material, preferably Nitinol.

Figure 9:
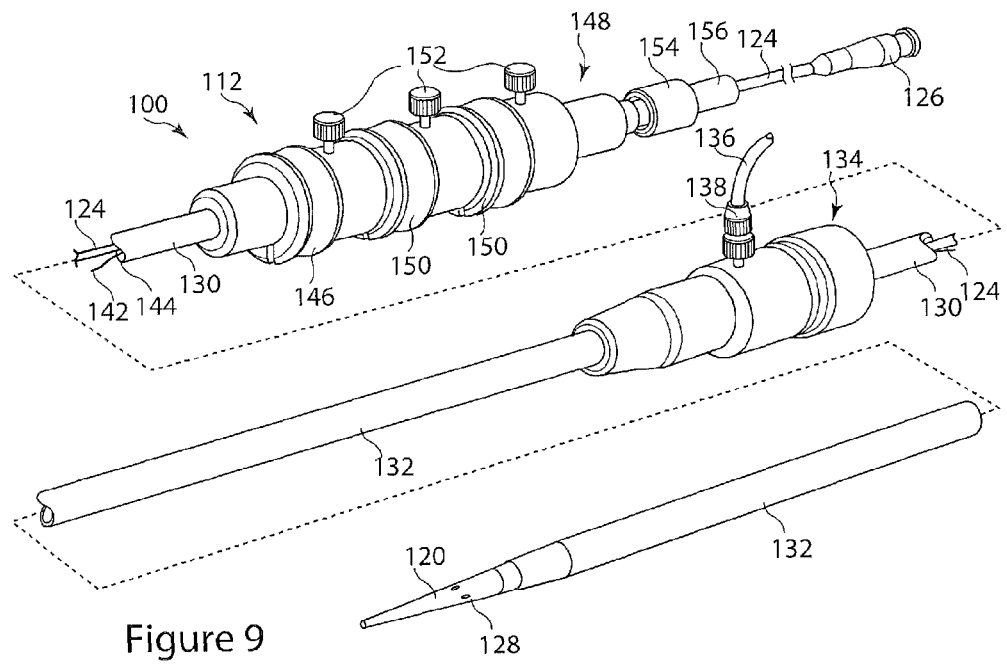
FIGS. 9 and 10 are exploded views of an embodiment of introducer assembly for the stent graft of FIG. 2.
Figure 10:
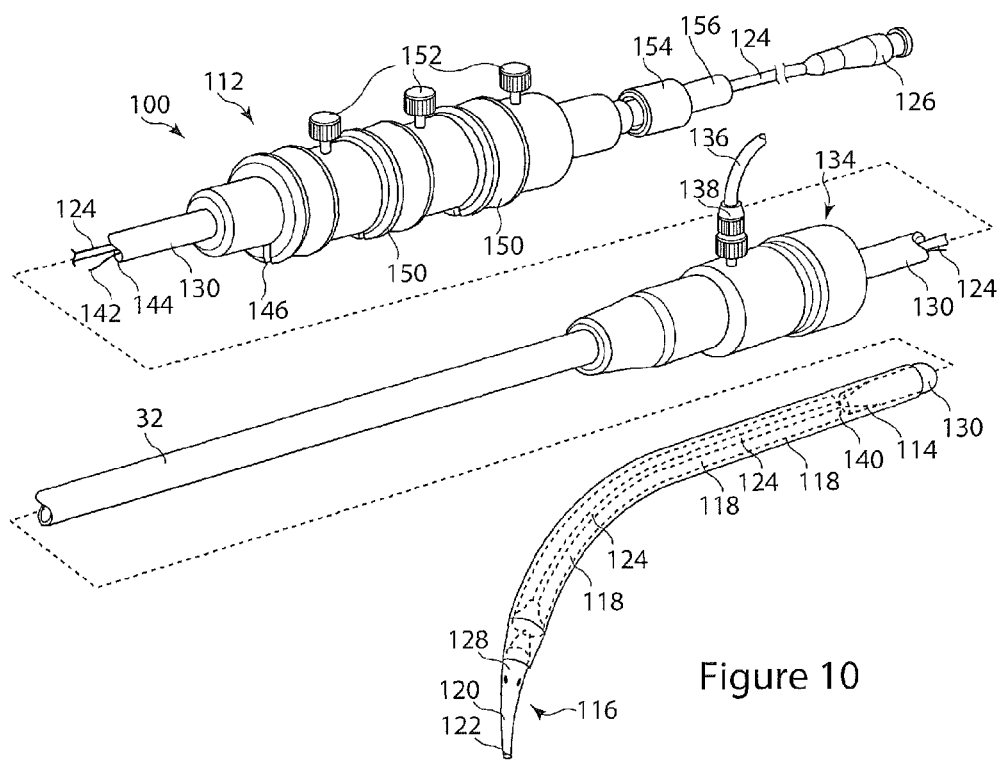

Referring now to FIGS. 9 and 10, there is shown an embodiment of introducer assembly for deploying the stent graft 40 shown in FIGS. 1 to 8. The introducer 100 includes an external manipulation section 112, a distal attachment region 114 and a proximal attachment region 116. The distal attachment region 114 and the proximal attachment region 116 secure the distal and proximal ends of the stent graft 118, respectively. During the medical procedure to deploy the stent graft 18, the distal and proximal attachment regions 114 and 116 will travel through the patient's lumen to a desired deployment site. The external manipulation section 112, which is acted upon by a surgeon to manipulate the introducer, remains outside of the patient throughout the procedure.

The proximal attachment region 116 of the introducer 110 includes a dilator tip 120, which is typically provided with a bore 122 therein for receiving a guide wire (not shown) of conventional type. The longitudinal bore 122 also provides a channel for the introduction of medical reagents. For example, it may be desirable to supply a contrast agent to allow angiography to be performed during placement and deployment phases of the medical procedure.

A guide wire catheter 124, conventionally made from a flexible thin walled metal tube, is fastened to the dilator tip 120. The guide wire catheter 124 is flexible so that the introducer 100 can be advanced along a relatively tortuous vessel, such as a femoral artery, and so that the distal attachment region 114 can be longitudinally and rotationally manipulated. The guide wire catheter 124 extends through the introducer 100 to the manipulation section 112, terminating at a connection device 126, in conventional manner.

The connection device 126 is designed to accept a syringe to facilitate the introduction of reagents into the inner catheter 124. The guide wire catheter 124 is in fluid communication with apertures 128 in the flexible dilator tip 120. Therefore, reagents introduced into connection device 126 will flow to and emanate from the apertures 128.

A pusher sheath or rod 130 (hereinafter referred to as a pusher member), typically made from a plastics material, is mounted coaxial with and radially outside of the guide wire catheter 124. The pusher member 130 is "thick walled", that is the thickness of its wall is preferably several times greater than that of the guide wire catheter 124.

A sheath 132 extends coaxially over and radially outside of the pusher member 130. The pusher member 130 and the sheath 132 extend distally to the manipulation region 112.

The implant 118, which in this embodiment is the stent graft 40, is retained in a compressed condition by the sheath 132. The sheath 132 extends distally to a sheath manipulator and haemostatic sealing unit 134 of the external manipulation section 112. The haemostatic sealing unit 134 includes a haemostatic seal (not shown) and a side tube 136 held to the unit 134 by a conventional luer lock 138.

The sheath manipulator and haemostatic sealing unit 134 also includes a clamping collar (not shown) that clamps the sheath 132 to the haemostatic seal and a silicone seal ring (not shown) that forms a haemostatic seal around the pusher rod 130. The side tube 138 facilitates the introduction of medical fluids between the pusher rod 130 and the sheath 132. Saline solution is typically used.

During assembly of the introducer 100, the sheath 132 is advanced over the proximal end of the dilator tip 120 of the proximal attachment region 116 while the implant 118 is held in a compressed state by an external force. A suitable distal attachment (retention) section (not visible in this view) is coupled to the pusher rod 130 and retains a distal end 140 of the prosthesis 118 during the procedure.

The distal end of the prosthesis 118 is provided with a plurality of trigger wires 142, 144. A proximal portion of the external manipulation section 112 includes at least one release wire actuation section 150 mounted on a body 148, in turn mounted onto the pusher member 130. The guide wire catheter 124 passes through the body 148. The trigger wire release mechanisms 146, 150 are mounted for slidable movement on the body 148.

A haemostatic seal (not shown) is included so that the release wires can extend out through the body 148 without unnecessary blood loss during the medical procedure.

A proximal portion of the external manipulation section 112 includes a pin vise 154 mounted onto the proximal end of the body 148. The pin vise 154 has a screw cap 156. When screwed in, vise jaws (not shown) of the pin vise 154 clamp against or engage the guide wire catheter 124. When the vise jaws are engaged, the guide wire catheter 124 can only move with the body 148 and hence it can only move with the pusher member 130. With the screw cap 156 tightened, the entire assembly can be moved together as one piece. Once the introducer assembly 112 is in the desired deployment position, the sheath 132 is withdrawn to just proximal of the distal attachment section 114.

Figure 11:
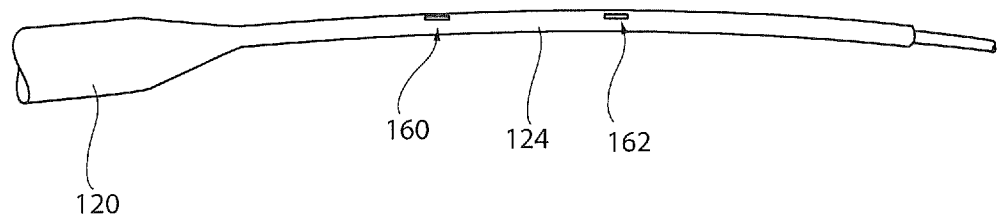
FIG. 11 is an enlarged view of the distal end of the introducer assembly of FIGS. 9 and 10.

Referring now to FIG. 11, there is shown the distal end of the introducer 100. The cannula 124 which carries the stent graft 40 is provided, in this embodiment, with first and second slots 160, 162 in its wall. The slots are sized to allow access to the trigger wires 142, 144 and in particular to allow coupling of the diameter reducing suture loops 58, 60 to the trigger wires.

In the preferred embodiment, there are provided three trigger wires 142, 144, which are arranged to be operated together. The trigger wires 142, 144 pass through the bore in the carrier 130 and by apertures at positions representative of the ends of the bare stents 44, 52 as well as at the diameter reducing suture loops 56, 58, 60. In this manner, the trigger wires can tie down, that is constrain radially, the stent graft 40 into the configuration shown in FIGS. 4 and 8. In practice, the stent graft 40 would be in a more longitudinally stretched condition than that shown in FIGS. 4 and 8, such that it would bulge outwardly less than shown in these drawings.

The outer sheath 132 covers the stent graft for the deployment procedure, thus pressing the entirety of the stent graft 40 against the carrier 124.

On deployment, once the distal end of the introducer 100 has been fed endoluminally to the treatment site, that is to the ascending aorta 22, the sheath 132 is pulled back, that is withdrawn, to expose the stent graft 40. Once released from the sheath, the stent graft 40 is able to deploy to its partly expanded position, shown in FIGS. 4 and 8. In this configuration, it is still possible to adjust the position of the stent graft 40 within the ascending aorta 22 to ensure its precise positioning. Once the surgeon is satisfied with this positioning, the trigger wires can be released. In the preferred embodiment, which uses three trigger wires operating in unison, the stent graft 40 is released from its proximal position first. That is, the proximal bare stent 44 is first released, whereupon it can flare outwardly. As the trigger wires continue to be withdrawn, the first diameter constraining loop 56 is then released, allowing the proximal end of the graft tube 42 to expand. In this configuration, it is still possible to adjust the position of the stent graft 40 and in particular to ensure that its proximal end avoids blocking the coronary arteries 26, 28 and that the bare stent 44 is made to sit at the aperture of the bulbous part 23 of the aorta.

In many instances, the stent graft 40 will abut against the false lumen walls and thus be partially held in place by these, until full deployment thereof.

The trigger wires are withdrawn further, releasing in sequence, the diameter reducing loops 58 and 60 and then the distal bare stent 52. Thus, the stent graft 40 is deployed in stages and in a manner that its position can be precisely adjusted.

Once the stent graft 40 has been deployed, the distal stent 70 is deployed in a second phase of the deployment operation, by expanding this such that its proximal end fits within the distal end of the stent graft 40, as shown for instance in FIG. 7.

As explained above, in other embodiments, the deployment sequence can be altered, particularly by providing additional trigger mechanisms. For instance, the distal bare stent 52 could be retained by a sleeve rather than the trigger wires, and thus deployable independently of the trigger wires. In another embodiment, there may be provided a plurality of sets of trigger wires, for instance two sets, each coupled to respective ones of the bare stents and diameter reducing loops, so as to be able to effect deployment of the bare stents and body of the graft tube in a sequence preferred by the surgeon or suited for a particular deployment procedure. For instance, in some circumstances it might be desired to deploy the body of the stent graft 40 before releasing the end of the stent graft, that is the bare stents 44, 52. In another example, it might be desired to deploy the stent graft 40 from its distal end first.

The invention claimed is:

1. A stent graft comprising:
    a graft tube provided with proximal and distal ends and first and second expanded configurations,
    a plurality of stent rings attached to the graft tube between the proximal and distal ends,
    a bare stent extending from the proximal end of the graft tube and designed to flare outwardly relative to the graft tube so as to engage in use a cavity of an aortic sinus of a patient,
    an intermediate stent ring having a proximal end and a distal end, the intermediate stent ring located between two other of the plurality of stent rings, and
    a mechanically releasable diameter restraining device comprising a first filament and a second filament, wherein the first and second filaments are positioned substantially half-way along the graft tube and at least partially inside the graft tube, and, when the graft tube is in the first expanded configuration, the first filament restrains the proximal end of the intermediate stent ring and the second filament restrains the distal end of the intermediate stent ring, such that in the first expanded configuration a diameter of the stent graft at the intermediate stent ring is less than a diameter of the stent graft at regions immediately proximal and distal the intermediate stent ring, and where stent rings immediately adjacent the intermediate stent ring are not restrained by a diameter restraining device when the graft tube is in the first expanded configuration, and
    wherein when the graft tube is in the second expanded configuration the mechanically releasable diameter restraining devices do not restrain any portion of the stent graft.

2. The stent graft of claim 1, wherein the stent graft is provided with a stent section extending from the distal end of the graft tube.

3. The stent graft of claim 1, further comprising a bare stent extending from the distal end of the graft tube.

4. The stent graft of claim 3, wherein the bare stent at the distal end flares outwardly relative to the graft tube.

5. The stent graft of 3, wherein each bare stent is formed of an undulating stent structure that has curved or apices.

6. The stent graft of claim 1, further comprising a second mechanically releasable diameter restraining device at the proximal end of the graft tube.

7. A stent graft comprising:
    a graft tube having proximal and distal ends, an intermediate position located approximately halfway between the proximal and distal ends, and first and second expanded configurations,
    a plurality of stent rings attached to the graft tube between the proximal and distal ends,
    a bare stent extending from the proximal end of the graft tube and designed to flare outwardly relative to the graft tube so as to engage in use a cavity of an aortic sinus of a patient,
    a first diameter restraining device comprising a first filament, the first diameter restraining device being located at or proximate the proximal end of the graft tube,
    a second diameter restraining device comprising a second filament, the second diameter restraining device located substantially half-way along the graft tube at the intermediate position of the graft tube between the proximal and distal ends of the graft tube, such that when the graft tube is in the first expanded configuration a diameter of the stent graft at the intermediate position of the graft tube is less than a diameter of the stent graft at regions immediately proximal and distal the intermediate position of the graft tube and where, in the first expanded configuration, the regions immediately proximal and distal the intermediate position are not restrained by a diameter restraining device, and
    where in the first expanded configuration the proximal end of the graft tube has a diameter less than the region immediately proximal the intermediate position of the graft tube, and wherein when the graft tube is in the second expanded configuration the diameter restraining devices do not restrain any portion of the stent graft.

8. The stent graft of claim 7, further comprising a stent at the distal end of the graft tube wherein at least a portion of the stent at the distal end of the tube extends from the distal end of the graft tube.

9. The stent graft of claim 7, further comprising a bare stent extending from the distal end of the graft tube.

10. The stent graft of claim 9, wherein the bare stent at the distal end flares outwardly relative to the graft tube.

11. The stent graft of claim 7, wherein the bare stent is formed of an undulating stent structure having curved apices.

12. The stent graft of claim 7, wherein the graft tube is in the region of 65 mm in length.

13. The stent graft of claim 7, wherein the bare stent extends from the graft tube by around 10 mm.

14. A stent graft comprising:
    a graft tube having a proximal end, a distal ends, a first expanded configuration and a second expanded configuration, the stent graft being of a length such that the graft tube does not block the coronary or brachiocephalic arteries when deployed,
    a plurality of stent rings attached to the graft tube between the proximal and distal ends, wherein one of the plurality of stent rings is disposed at an intermediate position along the graft tube between two other of the plurality of stent rings and has proximal and distal ends,
    a bare stent extending from the proximal end of the graft tube and designed to flare outwardly relative to the graft tube so as to engage in use a cavity of an aortic sinus of a patient,
    a first diameter restraining device comprising a first filament, and a second diameter restraining devices comprising a second filament and a third filament, the first diameter restraining device being located at or proximate the proximal end of the graft tube, the second diameter restraining device located at the intermediate position along the graft tube,
    wherein the filaments comprise diameter reducing loops disposed circumferentially around the graft tube, and
    wherein when the graft tube is in the first expanded configuration the second filament restrains the proximal end of the stent located at the intermediate position along the graft tube and the third filament restrains the distal ends of the stent located at the intermediate position along the graft tube such that a diameter of the stent graft at the intermediate position along the graft tube is less than a diameter of the stent graft at regions immediately proximal and distal the intermediate positioned along the graft tube and where the regions immediately proximal and distal the intermediate positioned along the graft tube are not restrained by a diameter restraining device, and wherein when the graft tube is in the second expanded configuration the diameter restraining devices do not restrain any portion of the stent graft.

15. A stent graft according to claim 14, wherein the distal end of the graft tube is provided with a stent and a portion of the stent at the distal end-extends from the distal end of the graft tube.

16. The stent graft of claim 14, further comprising a bare stent extending from the distal end of the graft tube.

17. The stent graft of claim 16, wherein the bare stent at the distal end flares outwardly relative to the graft tube.

18. The stent graft of claim 14, wherein the bare stent is formed of an undulating stent structure having curved apices.

19. The stent graft of claim 14, wherein the graft tube is in the region of 65 mm in length.

* * * * *